United States Patent
Hwang et al.

(10) Patent No.: US 7,635,362 B2
(45) Date of Patent: Dec. 22, 2009

(54) METHOD AND APPARATUS TREATING AREA OF THE SKIN BY USING MULTIPULSE LASER

(75) Inventors: Hae-Lyung Hwang, West Haven, CT (US); Glen Calderhead, Tochigi-Ken (JP)

(73) Assignee: Lutronic Corporation (KR)

( * ) Notice: Subject to any disclaimer, the term of this patent is extended or adjusted under 35 U.S.C. 154(b) by 679 days.

(21) Appl. No.: 11/321,387

(22) Filed: Dec. 28, 2005

(65) Prior Publication Data

US 2006/0149223 A1    Jul. 6, 2006

Related U.S. Application Data

(60) Provisional application No. 60/640,264, filed on Dec. 30, 2004.

(51) Int. Cl.
*A61B 18/18*    (2006.01)
(52) U.S. Cl. .................. 606/9; 606/1; 607/88
(58) Field of Classification Search .......... 606/3, 606/9, 10, 11–19
See application file for complete search history.

(56) References Cited

U.S. PATENT DOCUMENTS

| | | | | |
|---|---|---|---|---|
| 5,527,350 A | * | 6/1996 | Grove et al. ............... 607/89 |
| 5,643,252 A | * | 7/1997 | Waner et al. ............... 606/9 |
| 6,056,738 A | * | 5/2000 | Marchitto et al. ........... 606/2 |
| 6,080,147 A | * | 6/2000 | Tobinick .................... 606/9 |
| 6,096,029 A | * | 8/2000 | O'Donnell, Jr. ............. 606/9 |
| 6,106,514 A | * | 8/2000 | O'Donnell, Jr. ............. 606/9 |
| 6,120,497 A | * | 9/2000 | Anderson et al. ........... 606/9 |
| 6,149,645 A | * | 11/2000 | Tobinick .................... 606/9 |
| 6,162,211 A | * | 12/2000 | Tankovich et al. .......... 606/9 |
| 7,217,267 B2 | * | 5/2007 | Jay ........................... 606/18 |

* cited by examiner

*Primary Examiner*—Henry M Johnson, III
*Assistant Examiner*—Ronald Hunter
(74) *Attorney, Agent, or Firm*—Christie, Parker & Hale, LLP.

(57) ABSTRACT

The invention relates to a method and apparatus for multi-pulse laser treatments on a spot target by using a $CO_2$ laser system and a laser beam scanner attached at the end of the delivery system. The laser system is controlled to emit a laser macropulse consisting of a series of micropulses with pulse durations in the range of microseconds to a few milliseconds. The first group of pulses is delivered to cause minimal thermal damage to the peripheral area in the epidermis and dermis, while creating a pinhole epidermal window down into the dermis, through which the subsequent pulses, which are longer in pulse duration and lower in energy, deliberately create thermal diffusion through conducted heat to create thermal damage in the targeted area of the dermis.

12 Claims, 8 Drawing Sheets a   b   c a   b   c

METHOD AND APPARATUS TREATING AREA OF THE SKIN BY USING MULTIPULSE LASER

CROSS-REFERENCE TO RELATED APPLICATION

This application claims priority to and the benefit of U.S. Patent Application No. 60/640,264 filed in the United States Patent and Trademark Office on Dec. 30, 2004, the entire content of which is incorporated herein by reference.

BACKGROUND OF THE INVENTION (a) Field of the Invention

The present invention relates to a method and apparatus treating an area of skin using a multipulse laser. More particularly, the present invention relates to a method and apparatus that would enable the $CO_2$ laser beam to be delivered deep into dermis yet cause minimum thermal damage to the epidermal and superficial dermal tissue.

(b) Description of the Related Art

Since it was first invented in 1964, the $CO_2$ laser has been one of the most widely used surgical lasers. The $CO_2$ laser emits an infrared beam at 10,600 nm (nanometers). The beam is invisible to the human eye but has a uniquely high absorption characteristic in water molecules. Since human soft tissue is more than 70% water, the $CO_2$ laser is ideally suited to target the intracellular and extracellular water in the target tissue. When the water in the tissue absorbs laser light at 10,600 nm, the temperature of the tissue almost instantaneously increases until vaporization and ablation occur, surrounded by roughly concentric zones of coagulation, protein denaturation and athermal photobiomodulation, which can be seen clearly in stained histopathological specimens (refer to FIG. 7A).

Referring to FIG. 7B, changes in the staining pattern clearly show the different areas of damage. In a carbonization (Ca) area, tissue has been vaporized. In a coagulation (Co) area, where the tissue is literally cooked, very few cells will survive and most are already dead. In an area of protein denaturation (PD), there is a mixture of dead, damaged, and surviving cells. This zone is very important in starting the wound healing process. In an NT (normal-appearing tissue) area, consists of cells which have been directly stimulated by low photon density of laser energy exist and this layer is even more important for ensuring a good transition between the stages of wound healing.

Because of its efficacy in creating a layer of coagulative necrosis, by which small blood and lymphatic vessels are sealed, the $CO_2$ laser has become an ideal tool for bloodless surgery. In addition to incision and ablation, lowering of the incident power density of the $CO_2$ laser can also give selected nonablative effects.

In the middle of the 1990s, the $CO_2$ laser started to be used for scar revision and wrinkle removal. The water specific absorptive property of the $CO_2$ laser energy enables it to be used to ablate superficial tissue with the deposition of a controlled layer of residual thermal damage (RTD). The advantage of this method is that the tissue can be ablated layer by layer, with the RTD zone providing coagulation of small blood vessels thus giving a dry operative field. By adjusting the amount of energy delivered, the operator can control the depth of ablation to induce a deep or superficial peeling effect.

However, because the $CO_2$ laser ablates the epidermis and sometimes even goes down to the mid-dermis, over-aggressive $CO_2$ laser treatment has been associated with delayed healing time for reepithelialization. Even in cases of appropriate application, severe edema and crusting are seen in the immediately post-peel days with prolonged erythema and sometimes post inflammatory hyperpigmentation during the healing phase. After ablative $CO_2$ laser resurfacing, patients can experience weeks and sometimes months of recuperation time.

To overcome the disadvantages of ablative resurfacing for skin rejuvenation, nonablative resurfacing, known as nonablative skin rejuvenation, was developed. The newer methods use systems which employ shorter wavelengths than the $CO_2$ but that can still thermally damage the superficial and upper reticular dermis, but they do so under an intact epidermis which is aggressively cooled with, for example, a cryogen spray or contact cooling with a cooled sapphire lens. This technique enables selective cooling of the epidermis so that when the laser is fired onto the skin, and as the tissue absorbs the laser energy, the epidermal temperature is maintained at levels below the thermal damage threshold. So in effect, the dermis is heated and damaged but the epidermis is preserved. When the dermal wound is undergoing the wound healing process, the natural restorative effect of the intact epidermis can help to promote collagen regeneration and result in the desired rejuvenating effect. The essence of nonablative skin rejuvenation is controlled delivery of damage to the target dermis under an intact epidermis, so that none of the disadvantages of the ablative approach are experienced, and patient recuperation time is virtually nonexistent.

The limitation of current nonablative skin rejuvenation systems is that the laser must utilize some kind of cooling system. Furthermore, the main traditional wavelength for resurfacing, namely 10,600 nm of the $CO_2$ laser, can not be used due to its water absorption characteristics which limit the depth of penetration.

The contact cooling method cannot be effectively used for the $CO_2$ laser due to the presence of water condensation on the contact surface which would absorb the laser energy, and glass or quartz are actually opaque to that wavelength. In the cryogen spray cooling method, the cooling protects the epidermis, but the CO2 wavelength still does not allow sufficient penetration depth. The shallow penetration depth would limit the thermal damage required to be delivered to the deeper dermal regions and thus limit the collagen regenerative effect brought about by the wound healing process in tissue, which is well-recognized as being absolutely necessary for skin rejuvenation. As the $CO_2$ laser is an accepted modality as an ablative resurfacing tool, there is a need to create a system that enables the delivery of the $CO_2$ laser beam deep into the dermis yet produces non-ablative resurfacing clinical effects.

SUMMARY OF THE INVENTION

The present invention provides a method and apparatus that would enable the $CO_2$ laser beam to be delivered deep into dermis yet cause minimum thermal damage to the epidermal and superficial dermal tissue. According to an aspect of the invention, a method of treating an area of skin may include the steps of defining the area of skin as a target area for skin treatment, generating a laser beam in a macropulse from a $CO_2$ laser system, the macropulse having a first group of pulses and a second group of pulses with each of pulses in the second group having a longer pulse width than each of the pulses in the first group, forming a pinhole into the target area by directing the first group of pulses onto the skin, directing the second group of pulses into the pinhole, and generating a thermal wound in the deeper dermis of the target area.

The pulse width of each of the pulses in the first group may be adjusted to be shorter than a TRT (Thermal Relaxation Time) of skin tissue in the target area.

The pulse width of each of the pulses in the second group may be adjusted to be longer than a TRT of skin tissue in the target area.

Each of the pulses in the first group may have a pulse width in a range of 50 µs to 1000 µs and a pulse energy in a range of 5 mj to 500 mj.

Each of the pulses in the second group may have a pulse width in a range of 500 µs to 5000 µs and a pulse energy in a range of 5 mj to 500 mj.

The skin treatment is applicable to the treatment of skin conditions comprising treatments of abnormalities related to the dermis of skin.

The macropulse may be delivered to the target area either in a sequence of single pulses or in a sequence of multiple pulses.

A spot size when the second group of pulses is directed onto the target area may be the same as or smaller than the spot size when the first group of pulses is directed onto the target area. Specifically, each of the pulses in the first group has a pulse width in the range of 50 µs to 1000 µs, a spot size when the first group of pulses is directed onto the target area is in the range of 10 µm to 200 µm, and each of the pulses in the second group has a pulse width in the range of 500 µs to 5000 µs.

According to another aspect of the invention, an apparatus for treating an area of skin includes a housing having a laser beam source for generating and emitting a $CO_2$ laser, a set of user-set controls for adjusting a pulse width and a pulse energy of a laser beam pulse emitting from the laser beam source in compliance with external inputs and converting the laser beam pulse into a macropulse having a first group and a second group of pulses, each of the pulses in the second group having a longer pulse width than each of the pulses in the first group, a beam delivery system coupled to the housing and transferring the macropulse toward an area of skin, and a scanner mounted to an end of the beam delivery system and directing the macropulse onto the area of skin.

The scanner may have a supporting member to hold the scanner in a stable condition during the laser beam emission.

The supporting member may be a stabilizer leg or guide.

DETAILED DESCRIPTION

Embodiments of the present invention now will be explained with reference to the drawings.

Figure 1A:
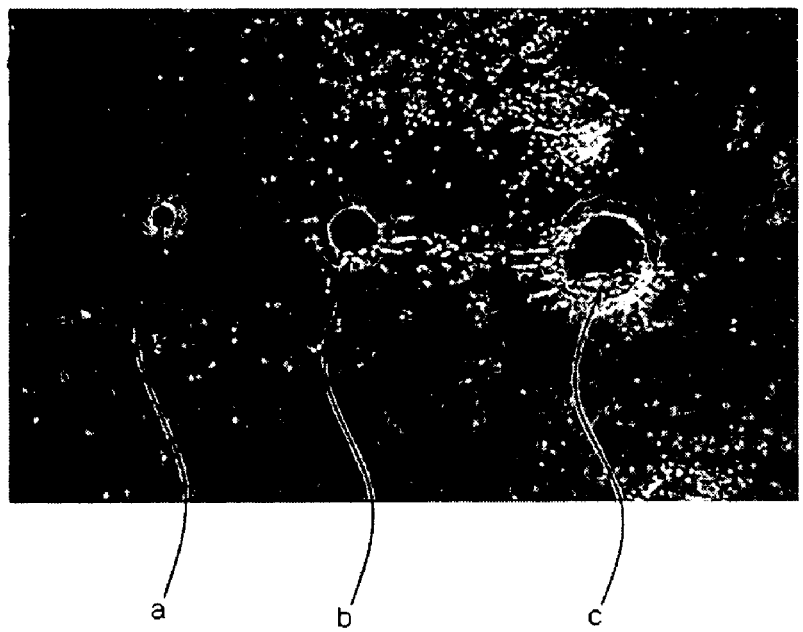
FIG. 1A is a photograph of a freshly excised pig liver showing the bioeffect of different $CO_2$ laser power energy densities.
Figure 1B:
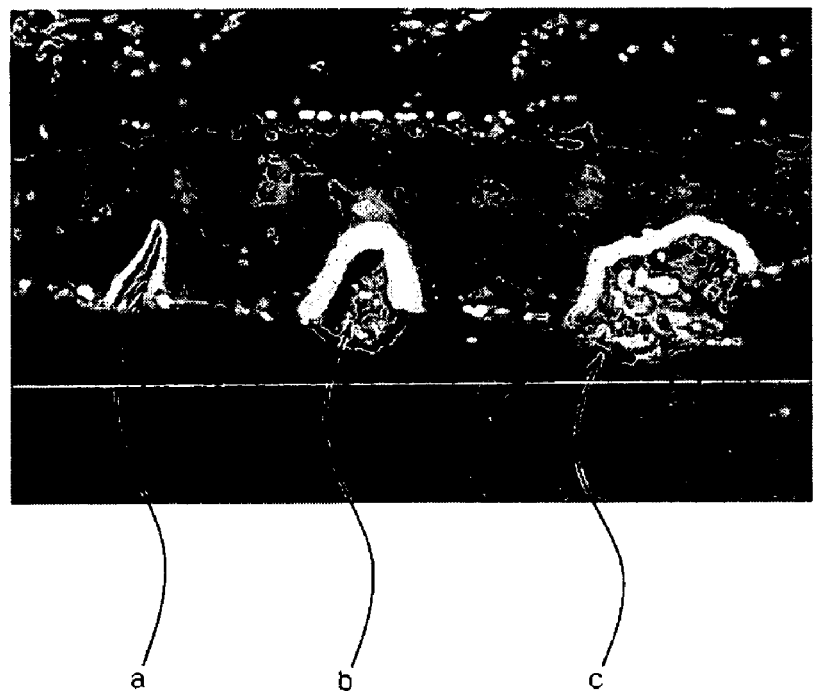
FIG. 1B is a macrophotograph of a freshly excised pig liver when an excision is made through the line of the holes in FIG. 1A.

FIG. 1A is a photograph of a freshly excised pig liver showing the bioeffect of different $CO_2$ laser power energy densities, and FIG. 1B is a macrophotograph of a freshly excised pig liver when an excision is made through the line of the holes in FIG. 1A.

Generally, the damage caused to living tissue by laser energy is related to how much heat is induced and how fast the energy is absorbed and converted into heat. If the laser induced heat is delivered over a longer period of time, a secondary wave of conducted heat can travel to the surrounding tissue and create secondary thermal damage. However, if the laser energy is delivered with very high peak power over an ultrashort pulse, then the heat created in the tissue does not have sufficient time to spread to surrounding area, and is limited to the target area only. Thus, limiting the laser pulse duration will decrease the peripheral thermal damage associated with conducted heat. Thermal relaxation time (TRT) of tissue is an amount of time it takes for target tissue to dissipate 50% of its heat to the surrounding area. In this case, if the laser beam is delivered for less than the TRT, then the heat does not have enough time be conducted to the surrounding tissue, thus causing less peripheral thermal damage. Depending on the characteristics of a laser system, selecting an ultrashort pulse and delivering a high peak power can specifically damage and vaporize target tissue with minimal secondary thermal damage to an area surrounding the target. On the other hand, the aim of the surgery might be coagulation of the target tissue, with or without ablative vaporization. In this situation, the pulse duration may be lengthened intentionally to create peripheral thermal damage sufficient to cause coagulation of the tissue surrounding the target.

Referring to FIG. 1A and FIG. 1B, spots a, b and c on the surface of the liver show the effect of doubling and redoubling the spot size of the laser beam while maintaining the same laser output power. That is, the laser irradiation time and output power remained constant, and only the spot size was changed. With spot 'a' there is a very small hole and mild peripheral damage; in spots 'b' and 'c' the hole gets progressively larger, as does the white change indicating coagulative change to the tissue surrounding the target area. In addition, as shown in FIG. 1B, pinhole "a" is the deepest with the least thermal damage, whereas pinhole "c" is the shallowest but is much wider ("a" to the left, "c" to the right). Pinhole "b" shows the greatest amount of thermal damage.

FIG. 2A to FIG. 2D are a schematic illustrations of the multipulse concept according to an exemplary embodiment of the present invention.

Figure 2A:
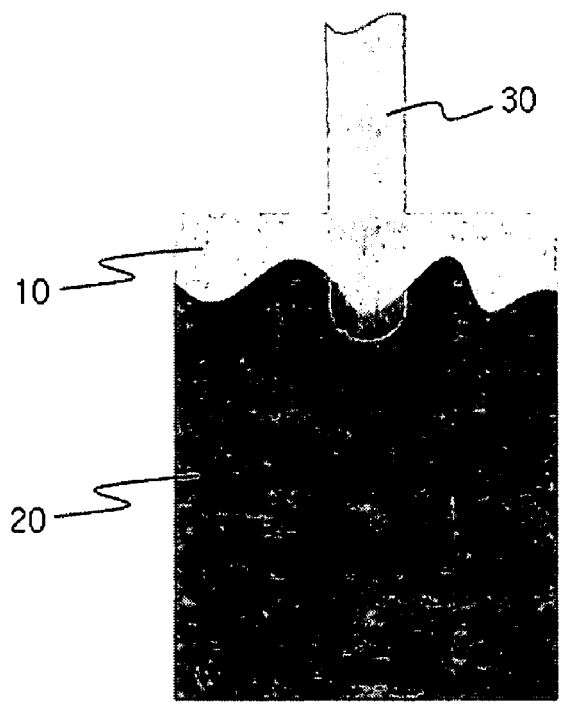
FIG. 2A to FIG. 2D are a schematic illustrations of the multipulse concept according to an exemplary embodiment of the present invention.
Figure 2B:
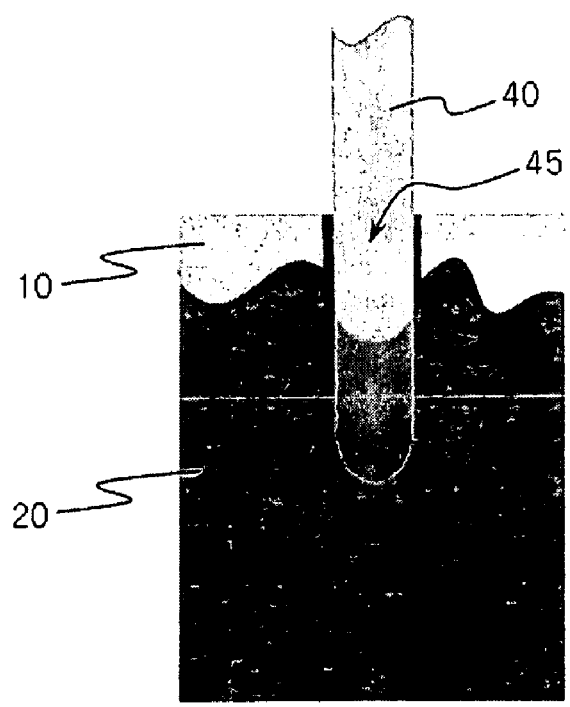
Figure 2C:
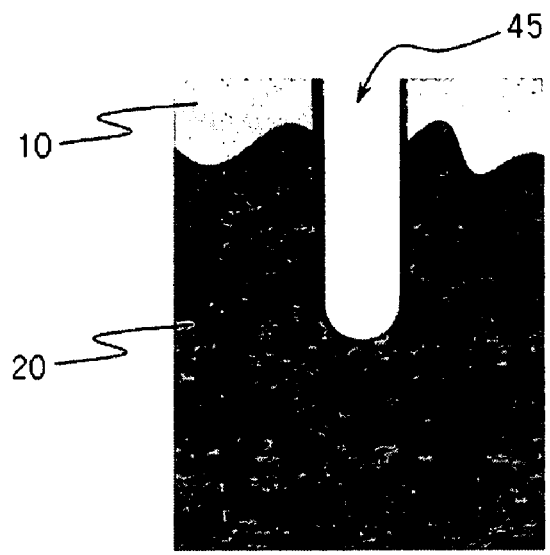
Figure 2D:
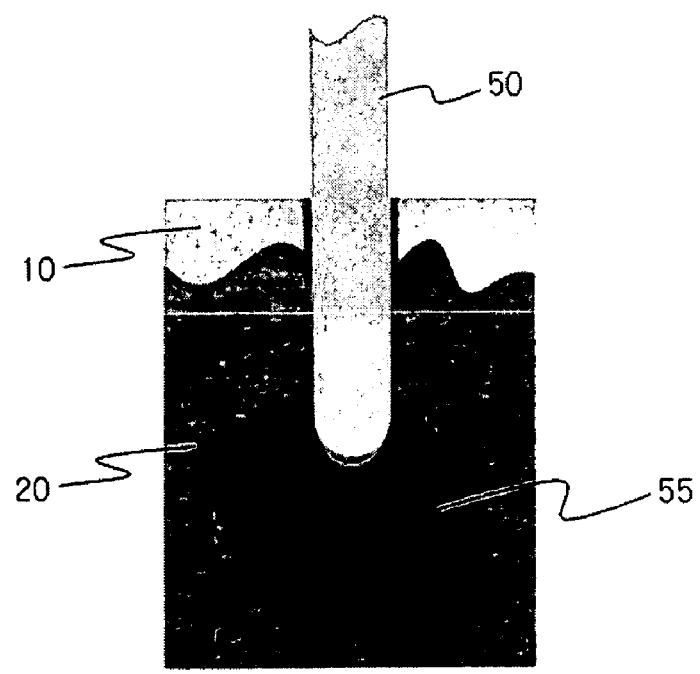

FIG. 2A shows a first micropulse 30 directing onto skin. FIG. 2B shows the second micropulse 40 with high energy density but a short pulse width that has penetrated into the dermis 20 through the epidermis 10, creating a pinhole 45 into which the second micropulse, with the same parameters, penetrates deeper into the dermis 20. FIG. 2C shows the pinhole 45 with access to the deeper dermis 20. This merely deepens the pinhole 45 without resulting in any more thermal damage in the pinhole 45. FIG. 2D shows a third micropulse 50 directing through the pinhole. The third micropulse 50 with a much longer pulse width, and therefore much less energy density but the same spot size, has entered through the pinhole 45 and created a controlled bolus 55 of thermal damage at the bottom of the pinhole 45 which has involved a much larger area of the dermis 20, while not disturbing the epidermis 10 and upper region of the dermis 20.

More specifically, referring to FIGS. 2A and 2B, a first micropulse 30 and the second micropulse 40, which are very short in duration, are sequentially directed onto an area of skin. For a $CO_2$ laser, if the beam has a very short pulse duration the peripheral thermal damaged can be minimized. If the spot size of the laser beam is maintained sufficiently small in size (less than 0.5 mm) then the epidermis will quickly reepithelize without scarring. At the same time, if the fluence is sufficiently high and the peak power of the laser is high, then a small laser beam would have a 'punching' effect into the skin, creating a small pinhole 45 in the epidermis 10, down into the dermis 20. This pinhole would have minimal thermal damage to the area surrounding it, but because of the high fluence of the laser beam the pinhole 45 would be sufficiently deep. A subsequent pulse with similar parameters on the same spot would allow the laser energy to pass through the pinhole 45 created in the epidermis 10 without damaging it further, but would cause additional ablation deeper into the dermis 20, with subsequent shots having an accumulative effect and creating a deeper hole. However, the thermal damage in the tissue surrounding the drilled hole would be minimal due the short pulse duration of the beam, until a slight defocusing of the beam lowers the incident power and energy densities. The effect of this multipulse method on the same treatment spot would be to continuously drill a pinhole into the skin the size of the laser spot.

However, to accomplish this, the energy density (radiant flux) of the laser beam must be sufficiently high. If the maximum output power of the normal $CO_2$ laser is 25 W (watts) then the average pulse of laser energy in superpulse or char-free mode will be less than 12 mj (millijoules) per pulse. Since the incident energy density is directly related to the spot size and hence the power density (irradiance) at the target tissue, a sufficiently small spot size (0.2 mm or less) will create high energy densities (see Table 1 for an explanation of the very important connection between spot size and power density).

TABLE 1

Relationship between spot size, power density, and tissue effect for a beam of constant incident power (2.0 W).

| Spot size (Ø) | Incident Power | Power density (Approx.) | Potential bioeffect |
|---|---|---|---|
| 100 m | 2.0 W | 25,500 W/cm² | Incision, excision, ablation |
| 200 m | 2.0 W | 6,350 W/cm² | Vaporization |
| 1.0 mm | 2.0 W | 255 W/cm² | Nonablative coagulation |
| 2.0 cm | 2.0 W | 2.55 W/cm² | Athermal photobiomodulation |

A laser beam with an energy of 12 mj focused to a spot of 0.075 mm would result in an energy density of 254 J/cm². Furthermore, if the pulse duration of the laser beam is sufficiently less than the thermal relaxation time of the tissue, then minimal peripheral tissue damage is created while the ablative effect is directed deeper into the tissue (FIG. 2A, and FIG. 2B). The first sequence of micropulses thus creates a sufficiently deep hole through the epidermis into the dermis. A subsequent series of longer pulses, much longer than the tissue TRT, is then directed through the pinhole 45 into the deeper dermis 20, and deliberately creates a bolus 55 of thermal damage, while not affecting the tissue surrounding the pinhole 45 in the upper dermis 10 and epidermis 20 (FIG. 2C and FIG. 2D). So, in effect, this multipulse method, consisting of a macropulse made up the appropriate number of micropulses, creates an area of thermal damage in the deeper dermis 20 while preserving the epidermis 10 to a certain extent, in other words enabling the $CO_2$ laser energy to penetrate deep into the dermis 20 through a pinhole 10. If the hole size is sufficiently small, and is spaced appropriately, then some islands of viable epidermis will be left in addition to the epidermis invaginating the pilosebaceous units in the target area (hair follicle and sebaceous gland), both of which will assist in ensuring a swift reepithelization of the damaged epidermis, while the much larger area of residual thermal damage in the deep dermis will quickly start the skin's wound healing process, leading to good collagen synthesis and remodeling.

In the present embodiment, the first group of pulses include the first and second micropulses 30 and 40, and the pulse widths of the first and second micropulses 30 and 40 are below 1000 μs. Because the pulse widths of the pulses in the first group are below 1000 μs, minimum thermal damage is created in the target area. If the pulse widths of the pulses in the first group are greater than 1000 μs, the punching effect into the skin is generated insufficiently.

In addition, the pulse widths of the pulses in the second group in the present embodiment are in the range of 1000 μs to 5 ms, thereby creating a bolus 55 of thermal damage in the large area into the dermis 20. If the pulse widths of pulses in the second group are less than the 1000 μs, the bolus 55 of thermal damage cannot be sufficiently created. If the pulse widths of the pulses in the second group are greater than 5 ms, there is a disadvantage in that excessive energy of the laser beam is delivered to the dermis.

Furthermore, it is preferable that the pulses in the first group have pulse energies greater than 5 mj. If the pulse energy is below 5 mj, the pinhole might not be created in the epidermis.

In addition, the spot size of the first group of pulses is greater than or equal to the spot size of the second group of pulses. Specifically, the spot size in the present embodiment is in the range of 10 μm to 200 μm.

Figure 3:
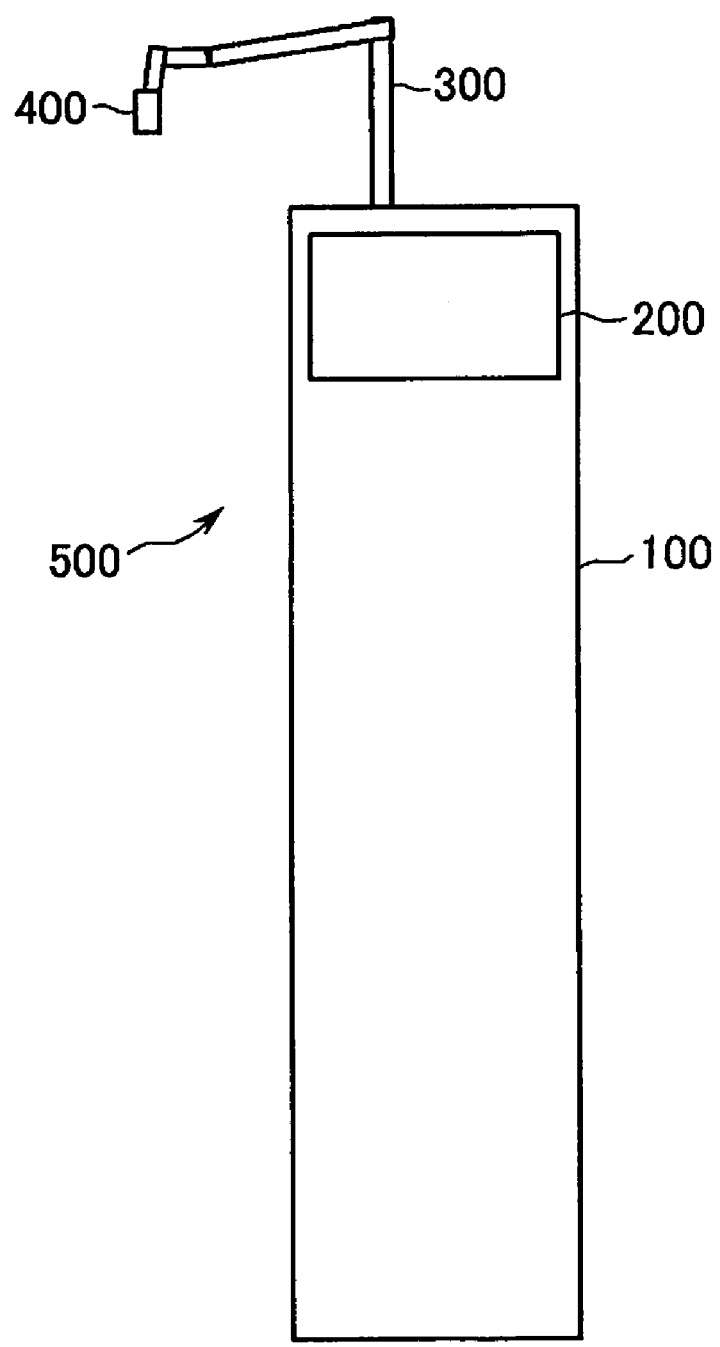
FIG. 3 is a schematic illustration showing the components of the laser treatment apparatus according to an exemplary embodiment of the present invention.
Figure 4:
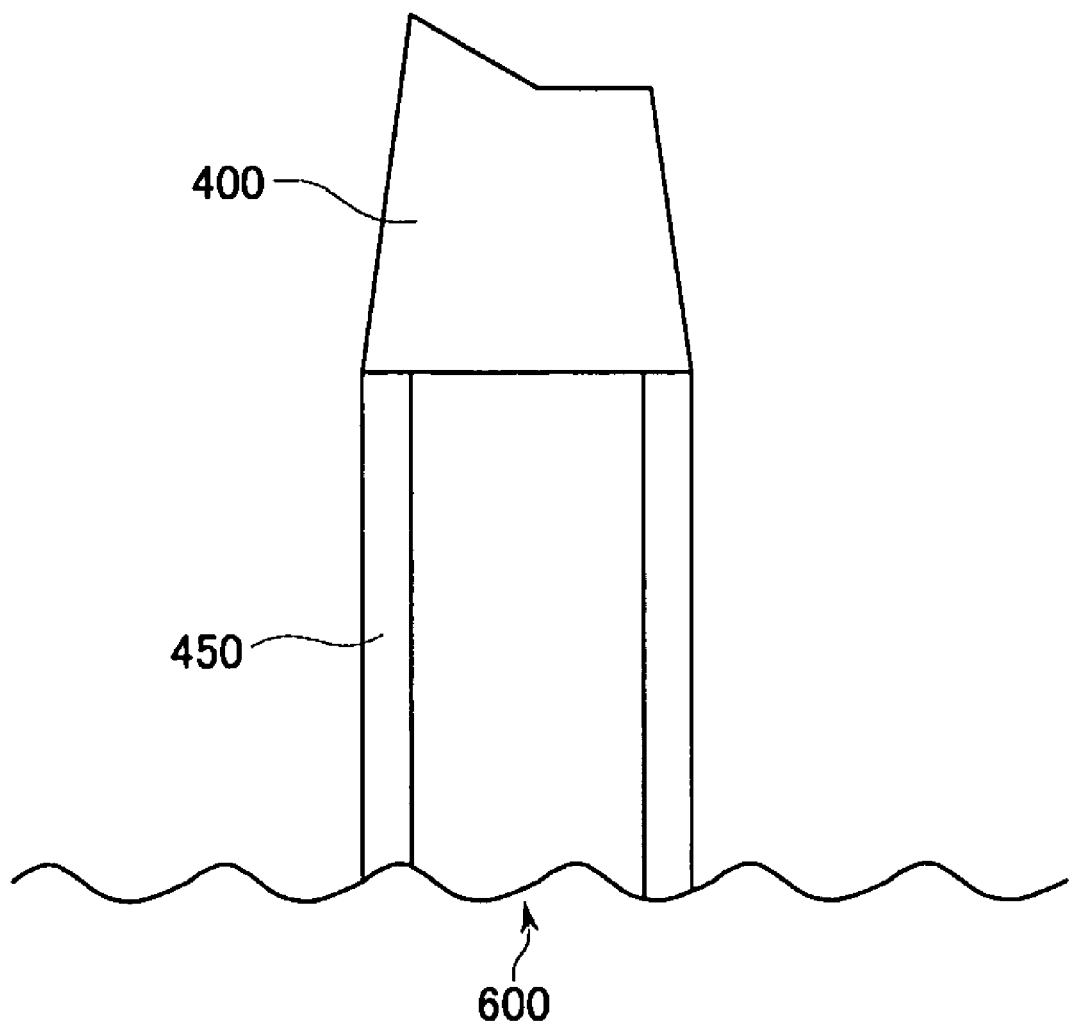
FIG. 4 is a schematic illustration showing supporting members for the scanner module according to an exemplary embodiment of the present invention.
Figure 5:
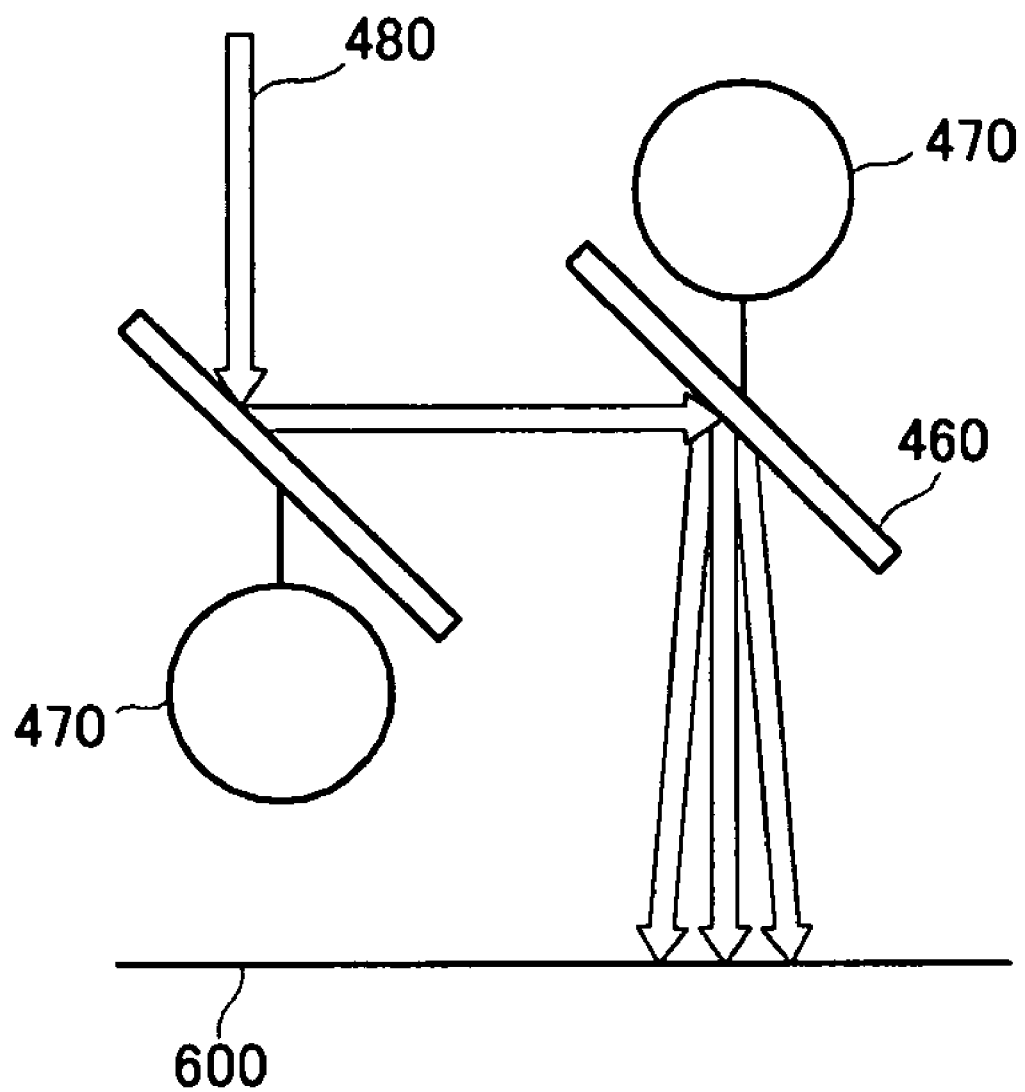
FIG. 5 is a schematic illustration showing the components of the scanner according to an exemplary embodiment of the present invention.

FIG. 3 is a schematic illustration showing the components of the laser treatment apparatus according to an exemplary embodiment of the present invention, FIG. 4 is a schematic illustration showing supporting members for the scanner module according to an exemplary embodiment of the present invention, and FIG. 5 is a schematic illustration showing the components of the scanner according to an exemplary embodiment of the present invention.

Referring to FIG. 3 to FIG. 5, the laser treatment apparatus 500 according to the exemplary embodiment of the present invention includes a housing 100, a set of user-set controls 200, a beam delivery system 300, and a scanner 400. The housing 100 includes a laser beam source (not shown in FIG. 3) that generates and emits a $CO_2$ laser beam. The set of user-set controls is mounted on the upper portion of the housing. The set of user-set controls has a pre-programmed microprocessor (not shown in FIG. 3). That is, when the information on the pulse width and the pulse energy of the laser beam is input through the user-set controls, the information is transferred to the pre-programmed microprocessor. Thus, by controlling the pre-programmed microprocessor, the pulse width and the pulse energy of the laser beam pulse emitting from the laser beam source can be adjusted in compliance with the external input, and the laser beam pulses can be converted into a macropulse having first and second groups of pulses.

Each of the pulses in the second group has a longer pulse width than each of the pulses in the first group. The beam delivery system 300 is coupled to the top portion of the housing 100, and transfers the macropulse toward the area of skin. In addition, a handpiece is coupled to the end of the beam delivery system 300 to direct the laser beam pulse onto the skin area.

Further, the efficacy of this method depends on a sufficiently short beam pulse in the initial train of pulses which is lower than the TRT of the target tissue, coupled with stability of the hand piece during delivery to maintain the beam on exactly the same target spot during the entire macropulse. To deliver laser energy with this method on a larger area, a scanner 400 is adapted to the laser handpiece. The scanner 400 has two reflective mirrors 460 or prisms which can direct the beam on to a predetermined spot. The two reflective mirrors 460 or prisms are controlled by galvanic motors 470, thereby controlling the direction of the laser beam 480. The operation of the scanner 400 is such that the scanner pauses at each spot so that the macropulse, with the stacked sequential micropulses, can be delivered on exactly the same spot. After each sequential beam delivery the scanner 400 is moved to the next spot. The scanner also has supporting members 450, such as stabilizer legs or guides, so that during the firing of the laser the hand piece or scanner cannot be easily moved on the skin surface 600.

Figure 6A:
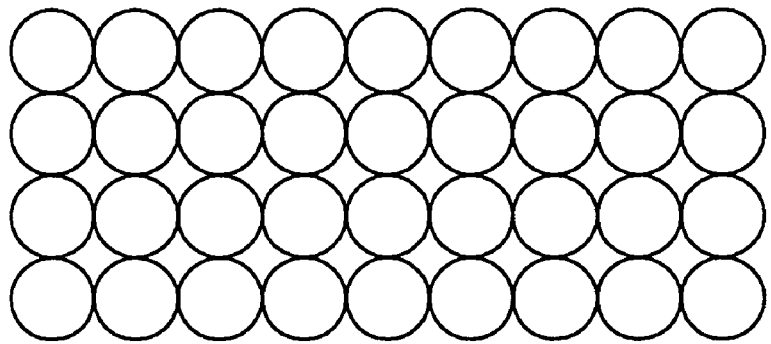
FIG. 6A to FIG. 6C are a schematic illustrations of the scanning mode in the multipulse delivery concept according to the exemplary embodiment of the present invention.
Figure 6B:
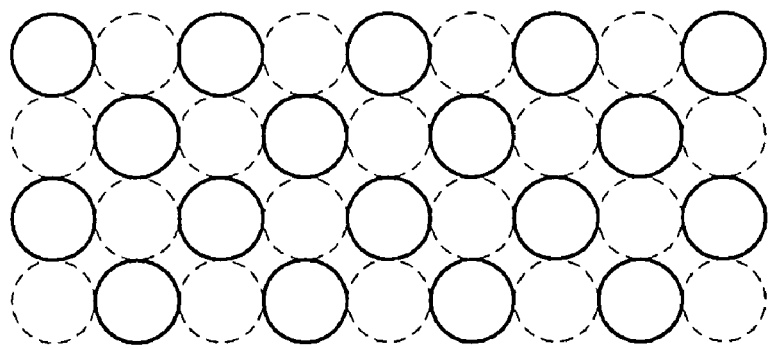
Figure 6C:
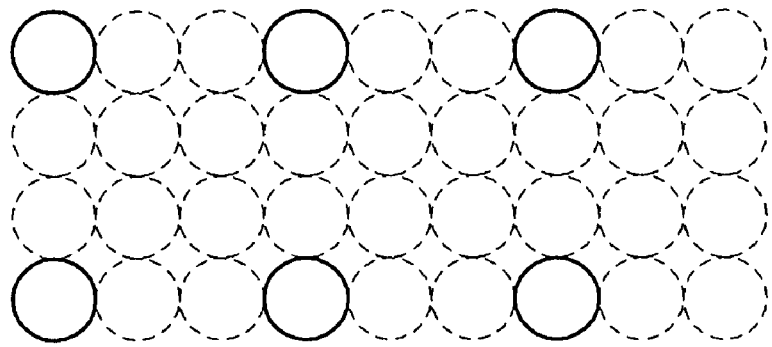
Figure 7A:
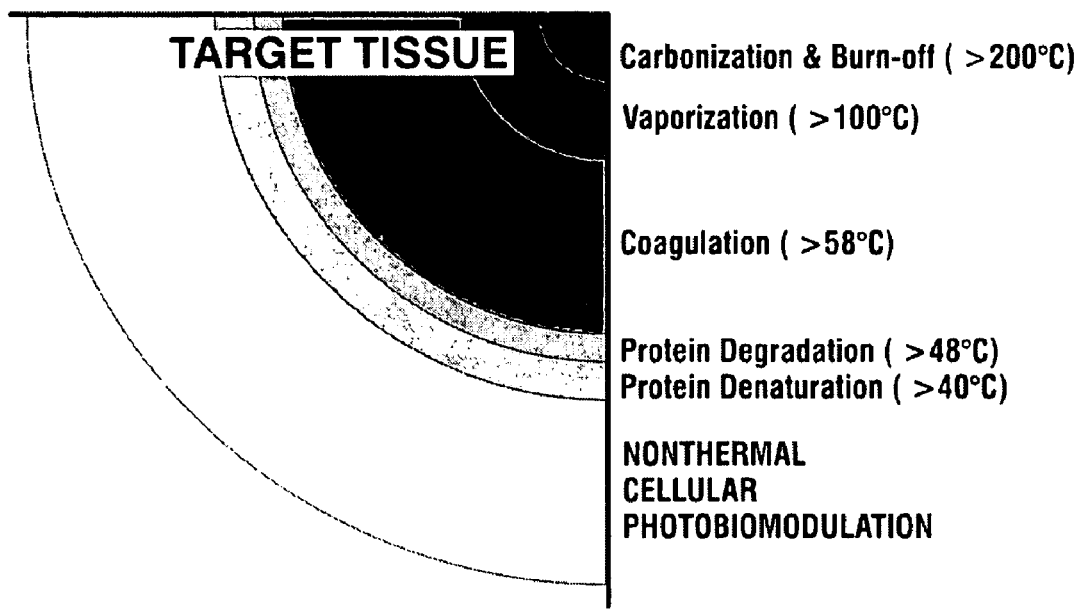
FIG. 7A is a view showing schematically concentric rings of temperature-dependent thermal damage diminishing with depth into human tissue.
Figure 7B:
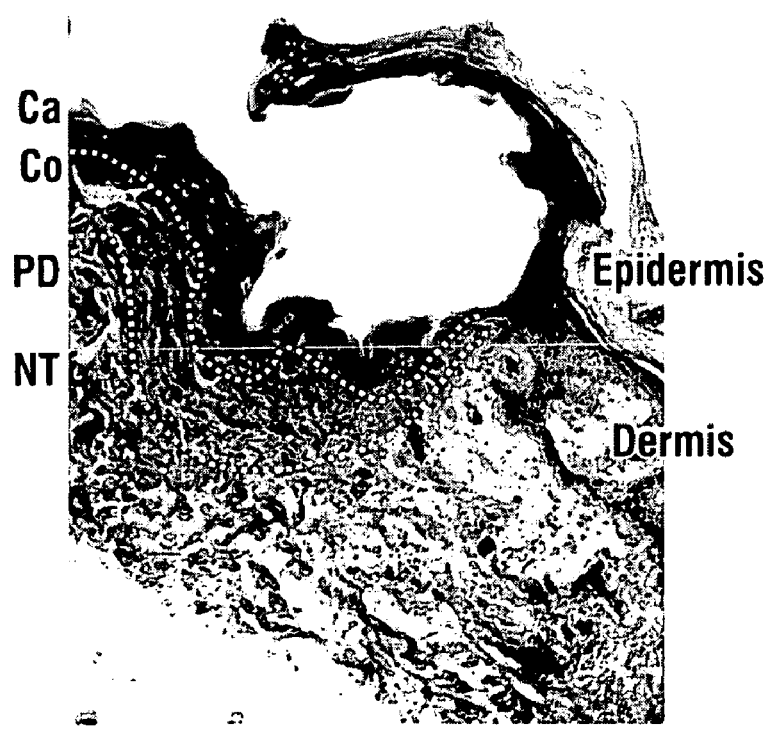
FIG. 7B is a photograph of an actual histological specimen of a single $CO_2$ laser shot in human tissue.

FIGS. 6A to 6C are schematic illustrations of the scanning mode in the multipulse delivery concept according to the exemplary embodiment of the present invention.

Referring to FIGS. 6A to 6C, the operation of the scanner function can be changed by altering the density of the irradiated area per spot. If each target spot is spaced adjacently, then this would give a 100% beam density. (FIG. 6A.), and would leave virtually no areas of untreated epidermis. However, if the beam is spaced apart and the distance between the spots is the same as the beam size, then the coverage of the scanner over the same area would be – (minus) 200%, and would leave greater areas of untreated epidermis between each individual spot (FIG. 6B). If the scanner is set to minus 300% coverage, then the distance between each treated spot would be 3 times the spot size, leaving even larger epithelial islands to assist with epithelization (FIG. 6C). The control of the scanner is accomplished by the scanner controller, which is typically microprocessor-based with user-friendly controls and LED (light-emitting diode) or LCD (liquid crystal display) indicators. At 100% density the effect of the treatment is similar to traditional ablative resurfacing as virtually no epidermis is preserved. However, with a decrease in beam density, some islands of epidermis are preserved. If the density of the treatment area is less, the volume of the thermal damage in the treated area is less, and although this will give excellent reepithelization, there will be less delivered thermal damage in the deeper dermis and thus less of a clinical effect seen in the treatment site.

Within the laser/scanner system integration, the pulse duration of each micropulse in the macropulse multishot sequence can be controlled. The controls on the laser enable the operator to reduce the various pulse widths to reduce the thermal damage for each pulse, or to increase the pulse width to deliberately create thermal damage in the deeper dermis during the last series of pulses.

The laser may be operated independently so that it is able to treat each target spot with a single shot as well as multiple shots over multiple target areas. The purpose of this is so that skin conditions such as active acne vulgaris can be treated with single sequential pulses which punch a hole into the acne, with the last pulse create thermolysis of the follicular plug and thermal sterilization of the deeper areas of the acne lesion in the hair follicle. For the treatment of wrinkles and other skin imperfections such as residual acne scarring, however, the scanning method is used and the density and size of the scan are controlled so that operator can determine both the intensity and size of the thermal damage delivered to the deeper dermis through the epidermal window as discussed above.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of treating an area of skin comprising the steps of:
    (a) defining the area of skin as a target area for skin treatment;
    (b) generating a laser beam in a macropulse from a $CO_2$ laser system, the macropulse having a first group of pulses having a first spot size and a second group of pulses having a second spot size, each of the pulses in the second group having a longer pulse width than each of the pulses in the first group, and said first spot size being greater than or equal to said second spot size;
    (c) forming a pinhole into the target area by directing the first group of pulses onto the skin;
    (d) directing the second group of pulses into the pinhole; and
    (e) generating a thermal wound in deeper dermis located within the pinhole.

2. The method of claim 1, wherein the pulse width of each of the pulses in the first group is adjusted to be shorter than a TRT (Thermal Relaxation Time) of skin tissue in the target area.

3. The method of claim 1, wherein the pulse width of each of the pulses in the second group is adjusted to be longer than a TRT (Thermal Relaxation Time) of skin tissue in the target area.

4. The method of claim 1, wherein each of the pulses in the first group has the pulse width below 1000 µs and a pulse energy over 5 mj.

5. The method of claim 1, wherein each of the pulses in the second group has the pulse width in a range of 1000 µs to 5000 µs.

6. The method of claim 1, wherein the skin treatment is applicable to the treatment of skin conditions comprising treatments of abnormalities related to a dermis of the skin.

7. The method of claim 1, wherein each of the pulses in the first group has a pulse width below 1000 µs, and wherein the first spot size is in the range of 10 µm to 200 µm.

8. The method of claim 7 wherein the second group of pulses has a pulse width in the range of 1000 µs to 5000 µs.

9. An apparatus for treating an area of skin, comprising:
    a housing having a laser beam source for generating and emitting a $CO_2$ laser beam;
    a set of user-set controls for adjusting a pulse width and a pulse energy of a laser beam pulse emitted from the laser beam source in compliance with external inputs, and converting the laser beam pulse into a macropulse, the macropulse having a first group of pulses having a first spot size and a second group of pulses having a second spot size, each of the pulses in the second group having longer pulse width than each of the pulses in the first group, and the first spot size being greater than or equal to the second spot size;

a beam delivery system coupled to the housing and transferring the macropulse toward the area of skin; and a scanner mounted to an end of the beam delivery system and directing the macropulse onto the area of skin.

10. The apparatus of claim 9, wherein the scanner has a supporting member for contacting a skin surface to hold the scanner in a stable condition during the laser beam emission.

11. The apparatus of claim 9, wherein each of the pulses in the first group has a pulse width below 1000 μs, and wherein the first spot size is in the range of 10 μm to 200 μm.

12. The apparatus of claim 11, wherein each of the pulses in the second group has a pulse width in the range of 1000 μs to 5000 μs.

* * * * *